United States Patent
Trehan et al.

(10) Patent No.: US 9,383,476 B2
(45) Date of Patent: Jul. 5, 2016

(54) IN-WELL FULL-BORE MULTIPHASE FLOWMETER FOR HORIZONTAL WELLBORES

(71) Applicant: WEATHERFORD/LAMB, INC., Houston, TX (US)

(72) Inventors: Sumeet Trehan, Standford, CA (US); Omer Haldun Unalmis, Kingwood, TX (US)

(73) Assignee: WEATHERFORD TECHNOLOGY HOLDINGS, LLC, Houston, TX (US)

( * ) Notice: Subject to any disclaimer, the term of this patent is extended or adjusted under 35 U.S.C. 154(b) by 494 days.

(21) Appl. No.: 13/934,332

(22) Filed: Jul. 3, 2013

(65) Prior Publication Data

US 2014/0012507 A1    Jan. 9, 2014

Related U.S. Application Data

(60) Provisional application No. 61/669,283, filed on Jul. 9, 2012.

(51) Int. Cl.
*G01V 11/00* (2006.01)
*G01F 1/74* (2006.01)
(Continued)

(52) U.S. Cl.
CPC ............. *G01V 11/002* (2013.01); *E21B 47/10* (2013.01); *G01F 1/34* (2013.01); *G01F 1/74* (2013.01);
(Continued)

(58) Field of Classification Search
CPC ..... G01V 11/002; G01F 15/024; G01F 5/005; G01F 1/34; G01F 1/74; E21B 49/08; E21B 47/00; G01N 33/2841; G01N 9/32; G01N 2291/02433; G01N 29/024; G01N 33/2823; G01N 9/26; G01N 2291/02809
USPC ................ 702/12, 100, 189; 73/61.45, 61.54, 73/861.63, 861.23, 861.04
See application file for complete search history.

(56) References Cited

U.S. PATENT DOCUMENTS

| 4,080,837 A | 3/1978 | Alexander |
| 4,114,439 A | 9/1978 | Fick |

(Continued)

FOREIGN PATENT DOCUMENTS

| CA | 2403616 A1 | 9/2001 |
| GB | 2266959 A | 11/1993 |

(Continued)

OTHER PUBLICATIONS

Search Report dated Sep. 7, 2007, issued by the British Patent Office in corresponding Application No. 0710273.4.

(Continued)

*Primary Examiner* — Carol S Tsai
(74) *Attorney, Agent, or Firm* — Patterson & Sheridan, L.L.P.

(57) ABSTRACT

Methods and apparatus for measuring individual phase fractions and phase flow rates in a multiphase flow based on velocity of the flow, speed of sound through the fluid mixture, and the density of the fluid mixture. Techniques presented herein are based on measuring frictional pressure drop across a flowmeter conduit, determining a surface roughness term for the conduit during initial flow tests or through other mechanical means, implementing a correction method to balance the momentum equation, and calculating the fluid mixture density using the measured pressure drop. The techniques may be applicable to measuring flow parameters in horizontally oriented conduits and, more generally, conduits of any orientation.

18 Claims, 11 Drawing Sheets

(51) Int. Cl.
*G01N 9/26* (2006.01)
*G01N 33/28* (2006.01)
*G01F 1/34* (2006.01)
*G01F 15/02* (2006.01)
*E21B 47/10* (2012.01)
*G01N 29/024* (2006.01)

(52) U.S. Cl.
CPC ............... *G01F 15/024* (2013.01); *G01N 9/26* (2013.01); *G01N 33/2823* (2013.01); *G01N 33/2841* (2013.01); *G01N 33/2847* (2013.01); *G01N 29/024* (2013.01); *G01N 2291/02433* (2013.01); *G01N 2291/02809* (2013.01)

(56) References Cited

U.S. PATENT DOCUMENTS

| | | | |
|---|---|---|---|
| 4,402,230 A | 9/1983 | Raptis | |
| 4,815,843 A | 3/1989 | Tiefenthaler | |
| 4,856,321 A | 8/1989 | Smalling | |
| 4,856,344 A | 8/1989 | Hunt | |
| 4,950,883 A | 8/1990 | Glenn | |
| 5,025,160 A | 6/1991 | Watt | |
| 5,115,670 A | 5/1992 | Shen | |
| 5,167,149 A | 12/1992 | Mullins | |
| 5,201,220 A | 4/1993 | Mullins | |
| 5,654,551 A | 8/1997 | Watt | |
| 5,831,743 A | 11/1998 | Ramos | |
| 5,956,132 A | 9/1999 | Donzier | |
| 6,023,340 A | 2/2000 | Wu | |
| 6,076,049 A | 6/2000 | Lievois | |
| 6,292,756 B1 | 9/2001 | Lievois | |
| 6,354,147 B1 | 3/2002 | Gysling | |
| 6,435,030 B1 | 8/2002 | Gysling | |
| 6,450,037 B1 | 9/2002 | McGuinn | |
| 6,463,813 B1 | 10/2002 | Gysling | |
| 6,532,826 B1 | 3/2003 | Dou | |
| 6,550,342 B2 | 4/2003 | Croteau | |
| 6,611,319 B2 | 8/2003 | Wang | |
| 6,655,221 B1 | 12/2003 | Aspelund | |
| 6,672,163 B2 | 1/2004 | Han et al. | |
| 6,683,681 B2 | 1/2004 | DiFoggio | |
| 6,691,584 B2 | 2/2004 | Gysling | |
| 6,785,004 B2 | 8/2004 | Kersey | |
| 6,850,317 B2 | 2/2005 | Mullins | |
| 6,879,386 B2 | 4/2005 | Shurgalin | |
| 6,898,541 B2* | 5/2005 | Gysling | G01F 1/74 702/100 |
| 6,945,095 B2* | 9/2005 | Johansen | E21B 47/10 73/61.45 |
| 6,995,352 B2 | 2/2006 | Hay | |
| 6,997,055 B2 | 2/2006 | DiFoggio | |
| 7,028,543 B2 | 4/2006 | Hardage | |
| 7,030,974 B2 | 4/2006 | Spirin | |
| 7,058,549 B2* | 6/2006 | Gysling | G01F 1/7082 702/189 |
| 7,142,306 B2 | 11/2006 | Wu | |
| 7,281,415 B2 | 10/2007 | Johansen | |
| 7,526,966 B2* | 5/2009 | Gysling | G01F 1/667 73/861.23 |
| 7,542,142 B2 | 6/2009 | Wu | |
| 7,587,948 B2 | 9/2009 | Gysling | |
| 7,603,916 B2* | 10/2009 | Gysling | G01F 1/36 73/861.42 |
| 7,654,155 B2* | 2/2010 | Johansen | G01F 1/44 73/861.63 |
| 7,880,133 B2 | 2/2011 | Johansen | |
| 8,003,932 B2 | 8/2011 | Sikora | |
| 8,061,186 B2* | 11/2011 | Gysling | G01N 29/024 73/61.54 |
| 8,339,591 B2 | 12/2012 | Volanthen | |
| 8,641,813 B2* | 2/2014 | Gysling | G01F 1/36 73/861.04 |
| 2004/0113081 A1 | 6/2004 | Hyde | |
| 2004/0139791 A1* | 7/2004 | Johansen | E21B 47/10 73/61.44 |
| 2004/0226386 A1* | 11/2004 | Gysling | G01F 1/7082 73/861.42 |
| 2005/0188771 A1 | 9/2005 | Lund | |
| 2005/0268702 A1* | 12/2005 | Johansen | E21B 47/10 73/61.45 |
| 2006/0186340 A1 | 8/2006 | Lievois | |
| 2007/0039380 A1* | 2/2007 | Charron | G01B 5/28 73/105 |
| 2007/0044572 A1 | 3/2007 | Davis | |
| 2007/0064218 A1 | 3/2007 | Montgomery | |
| 2007/0278408 A1 | 12/2007 | Johansen | |
| 2008/0236298 A1* | 10/2008 | Gysling | G01F 1/36 73/861.42 |
| 2010/0000333 A1 | 1/2010 | Volker | |
| 2010/0016689 A1 | 1/2010 | Kanayama | |
| 2011/0088462 A1 | 4/2011 | Samson | |
| 2011/0203386 A1 | 8/2011 | Johansen | |
| 2012/0152024 A1 | 6/2012 | Johansen | |

FOREIGN PATENT DOCUMENTS

| | | | |
|---|---|---|---|
| GB | 2397892 A | 8/2004 | |
| GB | 2442117 A | 3/2008 | |
| WO | 91/18280 A1 | 11/1991 | |
| WO | 2005/047908 A1 | 5/2005 | |
| WO | 2007/009097 A1 | 1/2007 | |
| WO | 2010/136810 A3 | 12/2010 | |

OTHER PUBLICATIONS

Examination Report dated Sep. 22, 2009, issued by the British Patent Office in corresponding Application No. 0710273.4.
Office Action dated Jul. 15, 2010, issued by the Canadian Intellectual Property Office in corresponding Application No. 2,590,996.
Office Action dated Aug. 1, 2013, issued by the Canadian Intellectual Property Office in corresponding Application No. 2,762,454.
Beck, M.S. "Correlation in instruments: Cross Correlation Flowmeters," Journal of Physics E: Instrument Sdence Technology; vol. 14, pp. 7-19 (1981).
European Search Report dated Nov. 1, 2013, issued by the Intellectual Property Office of Great Britain, in Application No. GB1312113.2.

* cited by examiner

US 9,383,476 B2

IN-WELL FULL-BORE MULTIPHASE FLOWMETER FOR HORIZONTAL WELLBORES

CLAIM OF PRIORITY UNDER 35 U.S.C. §119

This application claims benefit of U.S. Provisional Patent Application No. 61/669,283, filed Jul. 9, 2012 and entitled "In-Well Full-Bore Multiphase Flowmeter for Horizontal Wellbores," which is herein incorporated by reference in its entirety.

BACKGROUND

1. Field of the Invention

Embodiments of the present disclosure generally relate to determining phase component fractions and phase flow rates for a fluid mixture flowing in a conduit.

2. Description of the Related Art

In the petroleum industry, as in many other industries, ability to monitor flow of fluids in process pipes in real-time offers considerable value. Oil and gas operators measure individual oil/water/gas flow rates within an overall production flow stream containing a mixture of these three phase components. This information may be used to improve and optimize well production, allocate royalties, prevent corrosion based on the amount of water, and determine the well performance.

Production from gas wells may also include a significant liquid content (water, hydrocarbon oil, condensate, or combinations thereof). Flows with relatively high gas amounts with respect to liquid amounts (e.g., around or below 5% liquid by volume) are described as wet-gas flows and represent the high gas-volume-fraction (GVF) end of multiphase flows. Various prior flowmeters attempt to enable flow rate measurements or determinations of the phase components of these high-GVF flows using methodologies that are complex and difficult to implement, yet still yield only mixed results.

SUMMARY

Certain embodiments of the present disclosure provide a method for determining one or more flow rates of phase components of a fluid mixture in a conduit. The method generally includes measuring a bulk velocity and a speed of sound (SoS) of the fluid mixture; determining a differential pressure between two points in the conduit; calculating a density of the fluid mixture as a function of the differential pressure, the bulk velocity, and a surface roughness parameter associated with the conduit, and calculating at least one of phase fractions or the one or more flow rates of the phase components of the fluid mixture using the SoS, the bulk velocity, and the calculated density.

According to certain embodiments, the surface roughness parameter associated with the conduit was previously calculated based on differential pressure and bulk velocity measurements for a fluid flow having a known density. For some embodiments, the method may further involve periodically measuring differential pressure and velocity for the fluid flow having the known density and updating the surface roughness parameter associated with the conduit based on the periodically measured differential pressure and velocity. For other embodiments, the method may involve storing data regarding a change in the surface roughness parameter over time and adjusting a previously determined surface roughness parameter as a function of the elapsed time since the surface roughness parameter was last determined.

According to certain embodiments, calculating the density includes utilizing one or more theoretical fluid flow relationships that relate differential pressure of a fluid flow to bulk velocity, density, and a friction coefficient of the conduit based on the surface roughness parameter.

According to certain embodiments, the surface roughness parameter associated with the conduit was previously measured using a roughness measuring device. For some embodiments, calculating the density of the fluid mixture involves calculating a correction factor for the conduit to compensate for a discrepancy between measured fluid flow parameters and theoretical equations relating the parameters.

Certain embodiments of the present disclosure provide an apparatus for determining one or more flow rates of phase components of a fluid mixture in a conduit. The apparatus generally includes a processing system and a memory coupled to the processing system. The processing system is configured to determine a bulk velocity and a speed of sound of the fluid mixture; to determine a differential pressure between two points in the conduit; to calculate a density of the fluid mixture as a function of the differential pressure, the bulk velocity, and a surface roughness parameter associated with the conduit; and to calculate at least one of phase fractions or the one or more flow rates of the phase components of the fluid mixture, using the speed of sound, the bulk velocity, and the calculated density.

Certain embodiments of the present disclosure provide a computer-readable medium (e.g., a computer-readable storage device) for determining one or more flow rates of phase components of a fluid mixture flowing in a conduit. The computer-readable medium generally includes instructions which, when executed by a processing system, perform operations including measuring a bulk velocity and a speed of sound of the fluid mixture; determining a differential pressure between two points in the conduit; calculating a density of the fluid mixture as a function of the differential pressure, the bulk velocity, and a surface roughness parameter associated with the conduit; and calculating at least one of phase fractions or the one or more flow rates of the phase components of the fluid mixture, using the speed of sound, the bulk velocity, and the calculated density.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical aspects of this disclosure and are therefore not to be considered limiting of its scope, for the disclosure may admit to other equally effective embodiments.

DETAILED DESCRIPTION

Certain aspects of the present disclosure provide flowmeters that calculate individual phase flow rates of a multiphase flow based on three parameters: bulk velocity of the flow, speed of sound (SoS) through the flowing fluid mixture, and density of the fluid mixture. The bulk velocity and SoS may be obtained by direct measurements, but mixture density ($\rho_m$) is typically determined indirectly. For example, mixture density may be computed based on differential pressure between two points in a conduit (e.g., production tubing). For vertically displaced locations, given the change in height (Δh), the hydrostatic forces due to the weight of the fluid is usually more dominant than the friction forces on the fluid, and as a result, a more stable solution may be achieved for density. For horizontal applications, however, with little or no Δh, the friction forces on the fluid are the main driver for the calculation of density in accordance with aspects of the present disclosure.

The present disclosure provides techniques and apparatus for obtaining mixture density through measurements of differential pressure (e.g., between two pressure gauges) and the iterative use of this measurement in the fluid momentum equation. These techniques may be based on measuring the frictional pressure drop across a flowmeter, implementing a correction method to balance the momentum equation, and calculating the fluid mixture density using the measured pressure drop. The techniques may be suitable for making multiphase flow measurements using a full-bore conduit disposed horizontally, as well as in any other orientation.

Figure 1:
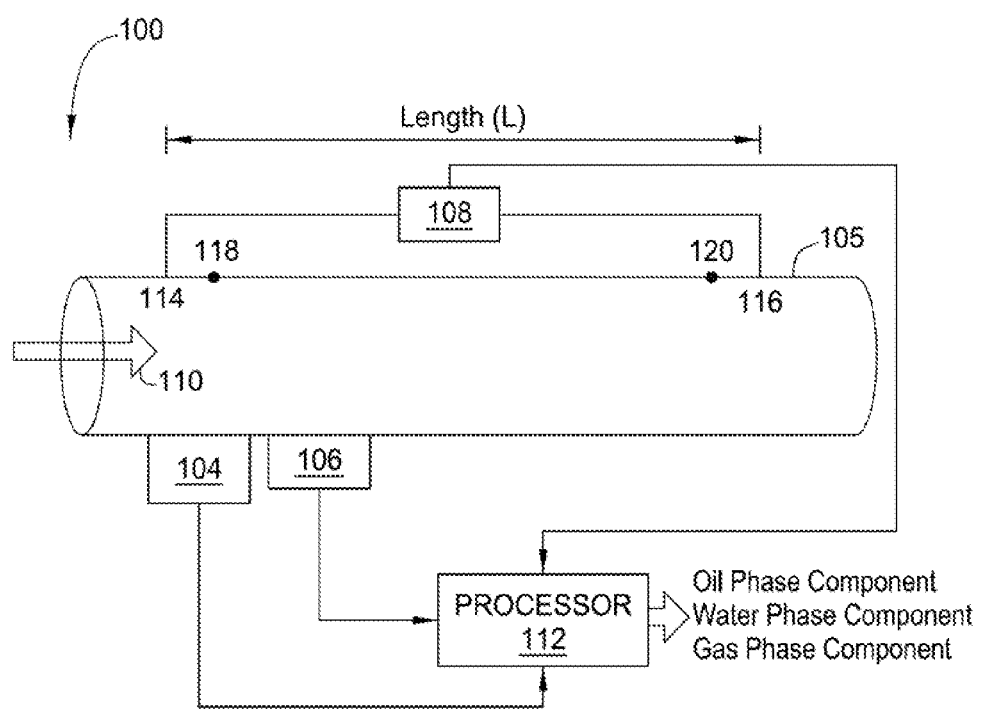
FIG. 1 shows a flow rate measuring system (flowmeter) according to embodiments of the present disclosure.

FIG. 1 illustrates an example system 100 that may be utilized to perform multiphase flow rate measurements of a fluid mixture flow 110 in a conduit 105 in accordance with aspects of the present disclosure.

As illustrated, the system 100 includes a differential pressure sensor 108 for measuring differential pressure between points 114 and 116 over a length L of conduit 105. The sensor may be any suitable type of sensor that measures differential pressure directly or uses the difference between absolute pressure measurements taken at two different points 114 and 116. The system 100 may also include one or more temperature sensors, which may be disposed at locations 118 and 120 for measuring the mixture temperature at or near the same points 114, 116 at which pressure is sensed by the differential pressure sensor 108. Pressure and temperature readings taken from the sensors may be used to quantify the component density and viscosity of the oil, water, and gas phases. The component density and viscosity of oil, water, and gas phases may then be used in an iterative algorithm which is explained in more detail below.

The system 100 may also include a fluid bulk velocity sensor 106 and a SoS meter 104 that allows measurement of SoS of the fluid mixture. In some cases, the SoS meter 104, the bulk velocity sensor 106, or both measurement devices may include a pressure sensor array.

An example of such a SoS meter 104 may include two or more sensing elements that form an array. Spacing between the sensing elements may enable sensing acoustic signals traveling at the SoS through the fluid flow 110 within the conduit 105 (referred to as "acoustic sensing") and can also enable sensing short duration local pressure variations traveling with the fluid flow (referred to as "flow velocity sensing"). The acoustic signals and/or the local pressure variations commonly originate from naturally occurring phenomenon. For some embodiments, the sensor elements may be formed with coils of optical fiber wrapped around the conduit 105. Other pressure measuring devices, such as piezoelectric or polyvinylidene fluoride (PVDF) based detectors, may also be used.

Certain examples of a bulk velocity sensor 106 may comprise multiple fiber-optic sensors disposed at different locations along the conduit 105. Naturally occurring pressure disturbances in the fluid perturb the first sensor through the wall of the conduit, creating a time-varying pressure signal. When the pressure disturbances (or pressure field) move from the first sensor to the second sensor, a similar pressure signal is measured. The two signals from the pressure sensors can then be cross-correlated to determine the time-shift in the pressure signals. This time-shift, when divided by the distance between the fiber-optic sensors, can be used to determine flow velocity. A processor 112 may receive signals indicative of the differential pressure, bulk velocity, SoS, and mixture absolute pressures and temperatures and may calculate phase fractions and/or volumetric phase flow rates of the fluid mixture flow 110 using processes based on principles described further herein.

Figure 2:
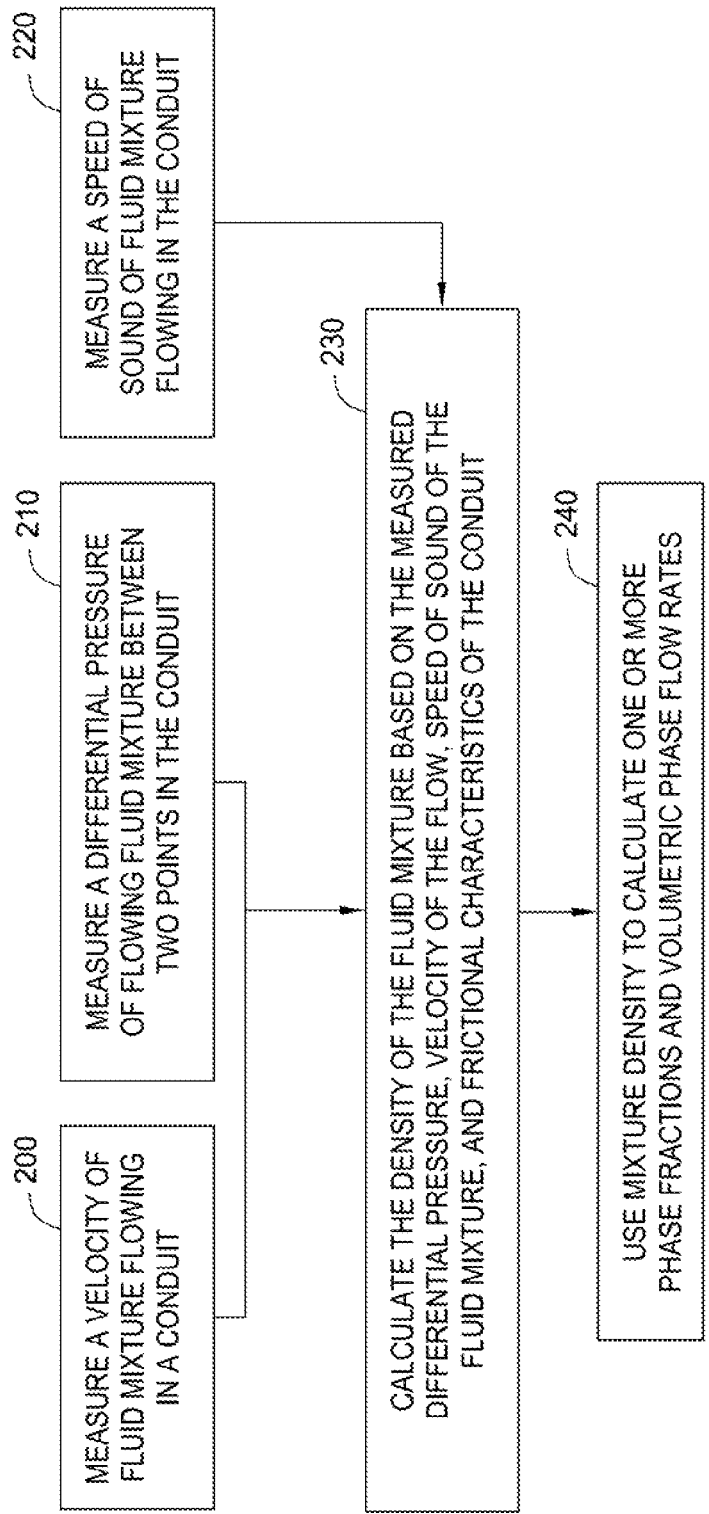
FIG. 2 is a flow diagram illustrating example operations for determining multiphase flow rates, in accordance with embodiments of the present disclosure.

FIG. 2 illustrates example operations for computing phase fractions and volumetric flow rates for each phase component, in accordance with certain aspects of the present disclosure. The operations may be performed utilizing the components shown in FIG. 1.

While the operations involve density of the flow, different techniques are presented for obtaining the density, with two such techniques described below with reference to FIGS. 3 and 5. Each of these techniques may involve a series of iterative computations that may be executed in accordance with steps depicted in FIG. 4.

Referring again to FIG. 2, at 200, bulk velocity of the fluid mixture flowing in a conduit is measured, for example, by the bulk velocity sensor 106 of FIG. 1. At 210, a differential pressure of the fluid flow is measured between (or calculated from separate measurements at) two points (e.g., across a length L), for example, by the differential pressure sensor 108 of FIG. 1. At 220, a SoS through the fluid mixture is measured, for example, by the sensor 104.

At 230, mixture density is calculated based on the bulk velocity, the differential pressure, the SoS, and values representing frictional characteristics of the conduit. The mixture density is used at 240 to compute one or more phase fractions and/or volumetric phase flow rates. The calculations at 230 and 240 may be performed by a processor, such as the processor 112 shown in FIG. 1. Any suitable slip model technique may be used in the mixture density and phase fraction calculations within the processor.

The determination of the frictional characteristics of the conduit and the utilization of this information at 230 and 240 may occur in accordance with various methodologies. Two example methodologies are explained with reference to FIG. 3 and FIG. 5 and discussed in greater detail below.

The use of mixture density to calculate volumetric phase flow rates, at 240, may also involve data obtained from the fluid bulk velocity sensor 106, which enables obtaining a measured bulk velocity ($V_{msrd}$) of the fluid mixture flow 110. As explained in greater detail in the following paragraphs, the measured bulk velocity ($V_{msrd}$) may be calibrated to adjust for measurement errors. The resulting calibrated mixture bulk velocity ($V_{cal}$) may be used, for example, by a slip model algorithm to determine the superficial phase velocities of the liquid ($V_{SL}$) and gas ($V_{Sg}$) components, which may have different velocities within the mixture.

In multiphase flow, the volumetric phase flow rates (Q) of the oil, water, and gas components may be calculated using Eqs. 1-3, respectively:

$$(Q_o)_{downhole} = A \cdot (1-\text{WLR}) \cdot V_{SL} \quad (1)$$

$$(Q_w)_{downhole} = A \cdot \text{WLR} \cdot V_{SL} \quad (2)$$

$$(Q_g)_{downhole} = A \cdot V_{Sg} \quad (3)$$

where A is the cross-sectional area of the conduit and where $V_{SL}$ and $V_{Sg}$ are the superficial liquid and gas phase velocities, respectively. The superficial velocity of a phase is defined as the velocity which would occur if that phase alone flows in the conduit. The water-in-liquid ratio (WLR) is the water volumetric flow rate relative to the total liquid volumetric flow rate at the pressure and temperature of the flow. Thus, computation of liquid and gas superficial phase velocities along with the WLR at the mixture pressure and temperature (as measured by the pressure and temperature sensors, such as those at points 114 and 118) enables volumetric flow rates of the phase components to be determined for a given conduit size.

Example Techniques for Determining Density, Holdup, and WLR

For some embodiments, the flowmeter calculates a density $\rho_m$ of the fluid mixture (herein, for simplicity, $\rho_m$ will also represent the density of a pure fluid when such a fluid is being measured in place of a fluid mixture) by measuring both a flow bulk velocity (V) and a differential pressure ($\Delta P$) of the flow. The flowmeter may be equipped with initial anticipated parameters for water-in-liquid ratio ($\text{WLR}^{(0)}$) and liquid holdup ($\text{HL}^{(0)}$) that represent baseline estimates of likely flow characteristics, given geologic conditions or other pertinent variables.

As illustrated, conduit 105 may lie along a section of pipe configured for fluid flow in the horizontal plane. In this case, because the differential pressure being measured is for a horizontal flow, any change in pressure is due to friction forces exerted by the pipe upon the fluid, rather than being primarily due to a change in vertical position. For the purpose of this disclosure, the flowmeter will be described assuming an orientation in the horizontal plane. Nonetheless, this disclosure and the principles discussed herein are equally applicable in the case of non-horizontal flows with an additional hydrostatic term that takes into account the gravitational forces, as explained above. For horizontal flows, the following momentum equation for fluid flow in a conduit may be applied:

$$\Delta P = \left(\frac{1}{2}\rho_m V^2\right)\left(\frac{L}{d}\right)f \quad (4)$$

where f is the friction coefficient of the conduit, L is the length of the portion of conduit for which the differential pressure is measured, d is the inner diameter of the conduit, and $\rho_m$ is the density of the fluid mixture.

The velocity term (V) in Eq. 4 represents the fictitious volumetric average flow velocity and is obtained by dividing the total volumetric flow rate with the cross-sectional area of the conduit. The velocity obtained by tracking the pressure disturbances (as explained above) through the conduit may or may not be equal to the volumetric average flow velocity. Hence a calibration process may be used to adjust for measurement errors as explained above.

The calibration process frequently involves the use of a similarity parameter that accounts for the changes in the physical parameters. One such similarity parameter in fluid dynamics is the Reynolds number (Re), which is a dimensionless number that represents the ratio of inertial forces to viscous forces. Given the volumetric average velocity of the flow, density and viscosity of the fluid mixture, and the size of the conduit, the Re may be calculated using the following formula:

$$Re = \frac{\rho_m V d}{\mu_m} \quad (5)$$

where V is the volumetric average velocity (equivalent to $V_{cal}$ in this context), $\rho_m$ is the mixture density, $\mu_m$ is the mixture dynamic viscosity, and d is the conduit diameter. It is expected that by calibrating based on Re, changes in fluid ($\rho_m$, $\mu_m$), flow (V), and geometry (d) can be captured.

When Re is used to calibrate the measured bulk velocity ($V_{msrd}$), a change in Re causes a change in the calibrated velocity ($V_{cal}$) even though the measured velocity may stay the same. Consequently, a change in fluid properties, such as density or viscosity, will trigger a change in the Re and, as a result, in the calibrated velocity. Thus, calibrated velocity may be recalculated after each iteration of fluid density.

A theoretical mixture density value may be obtained computationally based on Eq. 4, provided that differential pressure, bulk velocity, and a friction coefficient can be measured or determined. The friction coefficient can be modeled using one of the equations available in literature, such as Chen's Equation:

$$f = \left[-2\log\left(\frac{1}{3.7065}\left(\frac{\varepsilon}{d}\right) - \frac{5.0452}{Re}\log\left(\frac{1}{2.8257}\left(\frac{\varepsilon}{d}\right)^{1.1098} + \frac{5.8506}{Re^{0.8981}}\right)\right)\right]^{-2} \quad (6)$$

where $\varepsilon$ is the surface roughness parameter (a parameter determined exclusively by the material characteristics of the conduit) (Chen, N. H., "An Explicit Equation for Friction Factor in Pipe," *Ind. Eng. Chem. Fund.*, Vol. 18, No. 3, 296-97, 1979).

By substituting Chen's Equation (Eq. 6) into the momentum equation (Eq. 4), the flow of fluid in the pipe is theoretically modeled by the following relationship:

$$\Delta P = \left(\frac{1}{2}\rho_m V_{cal}^2\right)\left(\frac{L}{d}\right)\left[-2\log\left(\frac{1}{3.7065}\left(\frac{\varepsilon}{d}\right) - \frac{5.0452}{Re}\log\left(\frac{1}{2.8257}\left(\frac{\varepsilon}{d}\right)^{1.1098} + \frac{5.8506}{Re^{0.8981}}\right)\right)\right]^{-2} \quad (7)$$

It should be apparent that a reliable quantification of $\varepsilon$ therefore allows an iterative solution to the theoretical density of the fluid mixture to be determined, once bulk velocity and differential pressure are measured for a given conduit diameter, and the Re is known or calculated. Particular embodiments of the present disclosure are therefore dedicated to obtaining or utilizing a value for $\varepsilon$ that, when used in conjunction with Eq. 7, will enable a reliable density value for the fluid to be determined.

In one embodiment representing a first approach, illustrated in FIG. 3, a flowmeter may undergo initial tests under controlled flow conditions, typically a flow loop test, that enables the processor to calculate a value of the surface roughness parameter ($\varepsilon$) that is subsequently utilized during varied flow conditions of unknown fluid mixtures in order to accurately calculate mixture density. This embodiment allows accurate measurements of mixture density even in situations in which no attempt has been made to directly measure the surface roughness parameter.

Figure 3:
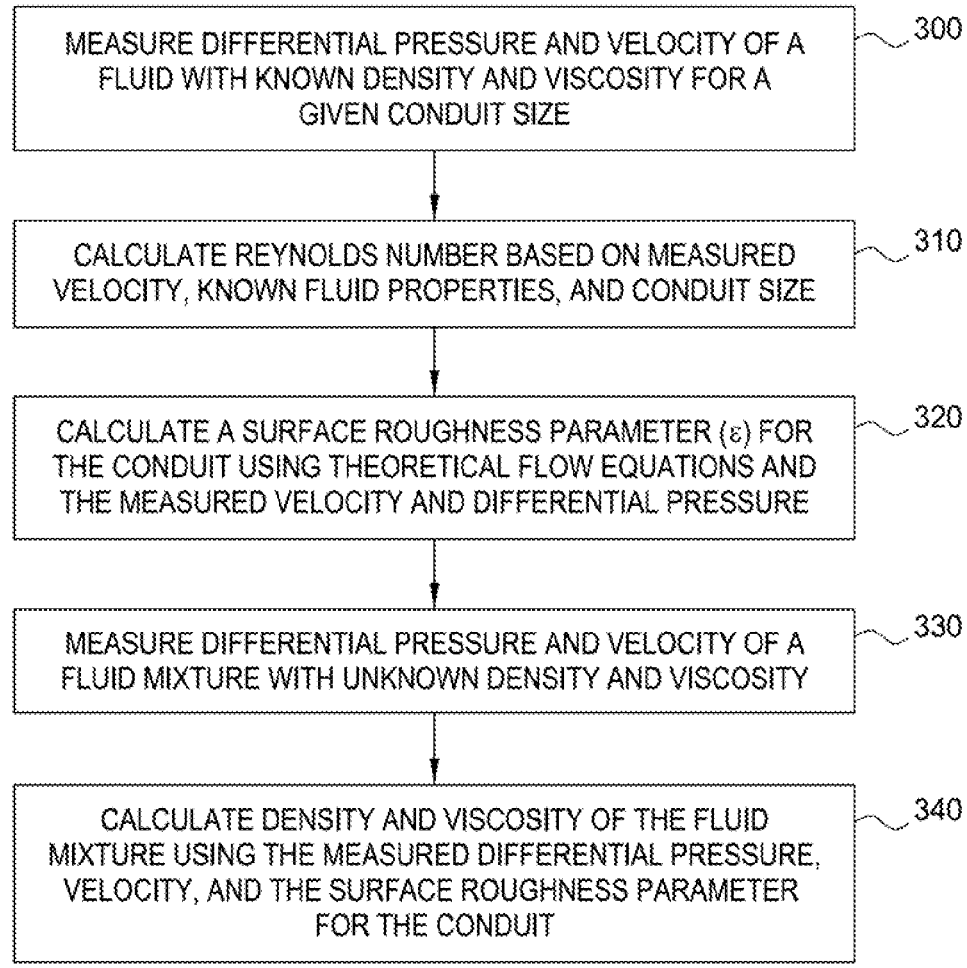
FIG. 3 is a flow diagram illustrating example operations for determining density, in accordance with embodiments of the present disclosure.

Referring to FIG. 3, at 300, the flowmeter measures bulk velocity and differential pressure of a fluid flow of known density and viscosity for a given conduit size. The Re is then calculated, at 310, using the measured and known quantities in accordance with the relationship provided above. Using theoretical equations in combination with known density, calculated Re, and the measured bulk velocity and differential pressure, the processor computes a surface roughness parameter, at 320, which represents the material characteristics of the conduit. At 330, the flowmeter is used to measure differential pressure and velocity of an unknown fluid mixture flow. At 340, the flowmeter uses the data measured at step 330, in combination with theoretical equations and the surface roughness parameter determined at 320, and the iterative technique explained in FIG. 4 to compute density for the unknown fluid mixture.

This first approach is generally formulated based on two foundational assumptions. The first assumption is that measured parameters of fluid flows processed by the flowmeter conform to Eq. 4 within reasonable bounds of error (mainly due to the uncertainties in modeling the friction factor in literature), such that the following relationship may be reliably employed:

$$\Delta P_{msrd} = \left(\frac{1}{2}\rho_m V_{cal}^2\right)\left(\frac{L}{d}\right)f \quad (8)$$

The second assumption is that Eq. 6 is sufficiently accurate to model the relationship between the parameters f, Re, and $\varepsilon$ for the fluid flows processed by the flowmeter. Thus, the design of the first embodiment applies the fundamental relationship in Eq. 4 and the modeling in Eq. 6 to all actually measured flows, thereby assuming that for all such flows, the following combined equation is applicable:

$$\Delta P_{msrd} = \left(\frac{1}{2}\rho_m V_{cal}^2\right)\left(\frac{L}{d}\right)\left[-2\log\left(\frac{1}{3.7065}\left(\frac{\varepsilon}{d}\right) - \frac{5.0452}{Re}\log\left(\frac{1}{2.8257}\left(\frac{\varepsilon}{d}\right)^{1.1098} + \frac{5.8506}{Re^{0.8981}}\right)\right)\right]^{-2} \quad (9)$$

The first approach may involve an experimental investigation of surface roughness in a flow loop test by measuring the bulk velocity and differential pressure of a fluid of known density ($\rho_{m,known}$) as it flows through the flowmeter conduit. An incompressible fluid, such as water, may be used for this process. The flowmeter may calculate (e.g., via processor 112) an experimental surface roughness parameter ($\varepsilon$) that satisfies Eq. 9 when that equation is applied to the measured ($\Delta P_{msrd}$, $V_{cal}$), known ($\rho_{m,known}$), and calculated (Re) values.

Because $\varepsilon$ is dependent only on the conduit material and not the fluid flowing through it, the experimentally determined value of $\varepsilon$ may be treated as a constant parameter suitable for future utilization by the processor for calculations of the mixture density of unknown fluid flows. The value of $\varepsilon$ is determined experimentally through flow tests and is expected to remain fairly constant for the life of flowmeter when corrosion and scale effects are ignored.

Following the experimental investigation of surface roughness, the flowmeter may be able to accurately calculate the mixture density for unknown fluid flows because the surface roughness parameter $\varepsilon$ is quantified. In these subsequent measurement processes, the flowmeter again measures differential pressure, mixture absolute pressure and temperature, bulk velocity, and SoS through the mixture. The processor may then apply the value of $\varepsilon$ to a series of iterative calculations that lead to mixture density and viscosity, liquid holdup, superficial liquid velocity, and superficial gas velocity.

Figure 4:
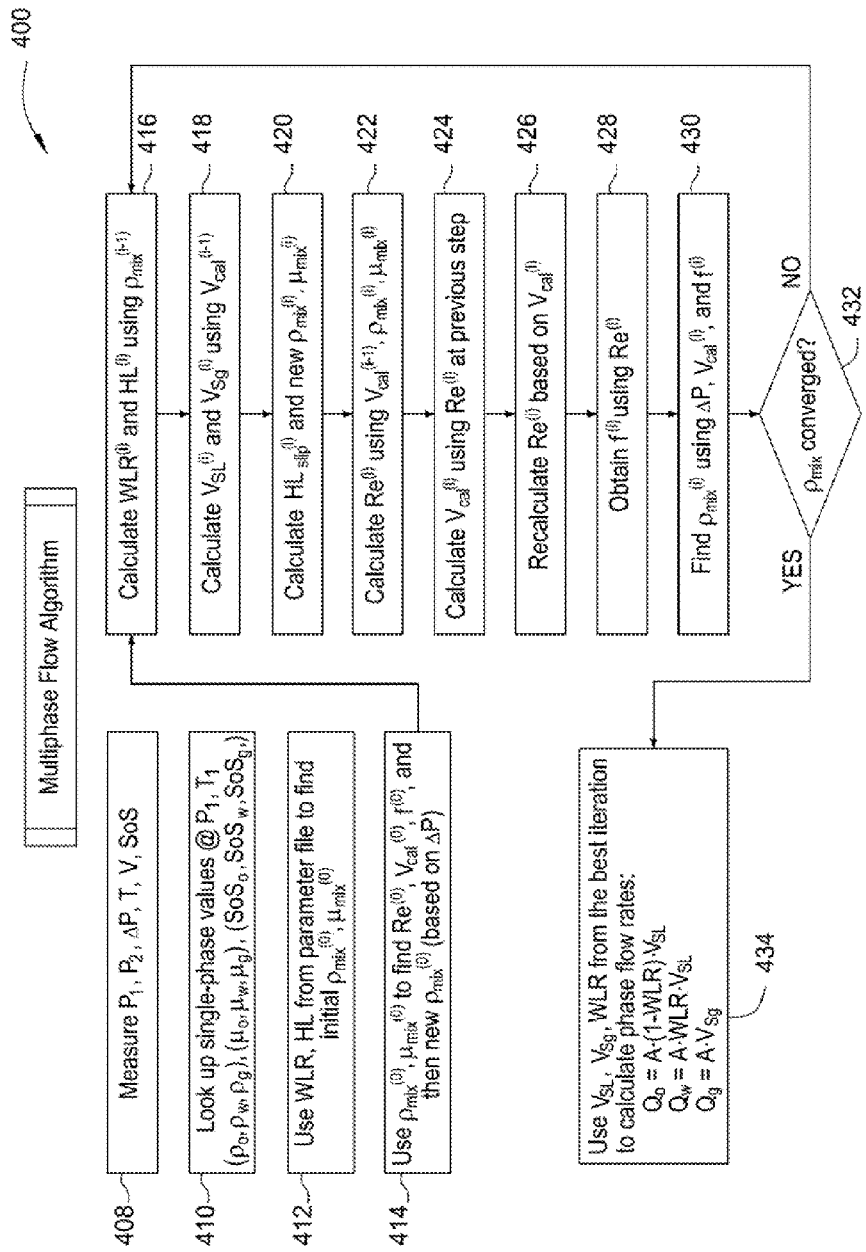
FIG. 4 is a flow diagram showing an example iterative technique that can be used to calculate mixture density and other flow parameters, in accordance with embodiments of the present disclosure.

FIG. 4 illustrates example operations 400 for an iterative multiphase flow algorithm that may be used to calculate the density of the fluid mixture. At 408, absolute pressure, differential pressure across a length of the conduit (or a second absolute pressure ($P_2$) across the conduit to obtain a differential pressure when used in conjunction with the first absolute pressure ($P_1$)), absolute temperature (T), bulk velocity (V) of the fluid flow, and SoS of the fluid mixture are measured using the techniques discussed in the description of FIG. 1.

At 410, the processor uses the absolute pressure and temperature measurements of the flow to determine the component density, viscosity, and SoS of the oil, water, and gas phases. These values may be stored in memory as one or more look-up tables, for example.

At 412, initial estimates of liquid holdup and WLR are used to calculate initial estimates of mixture density ($\rho_{mix}^{(0)}$) and viscosity ($\rho_{mix}^{(0)}$). As described above, the initial estimates for water-in-liquid ratio (WLR$^{(0)}$) and liquid holdup (HL$^{(0)}$) may represent baseline estimates of likely flow characteristics, given geologic conditions or other pertinent variables.

At 414, the initial estimates of mixture density and viscosity are used to compute an initial estimate of Re (Re$^{(0)}$). A calibrated flow velocity ($V_{cal}^{(0)}$) is obtained using this initial estimate of Re. Re is then recalculated with the calibrated flow velocity and is used in the computation of the initial friction coefficient (f$^{(0)}$). The initial fluid mixture density is then recomputed this time using the calibrated flow velocity, initial friction coefficient, and the measured differential pressure. At 416, the recomputed initial estimate of mixture density ($\rho_{mix}^{(0)}$, or $\rho_{mix}^{(i-1)}$ in the general case) is used to compute new values of WLR (WLR$^{(i)}$) and liquid holdup (HL$^{(i)}$).

At 418, the previously determined value of calibrated flow velocity ($V_{cal}^{(i-1)}$) is used in a slip model to calculate the superficial velocity of gas ($V_{Sg}^{(i)}$) and liquid ($V_{SL}^{(i)}$) phases within the mixture flowing in the conduit. At 420, the slip model is used to calculate refined values of liquid holdup ($HL_{slip}^{(i)}$), mixture density ($\rho_{mix}^{(i)}$), and mixture viscosity ($\mu_{mix}^{(i)}$). At 422, Re is recomputed ($Re^{(i)}$) using the most recently calculated values of mixture density and viscosity, along with the previously determined calibrated flow velocity. At 424, a refined calibrated velocity ($V_{cal}^{(i)}$) is determined using the Re calculated at 422. At 426, a refined Re is computed based on the refined calibrated velocity determined at 424. At 428, a refined friction coefficient ($f^{(i)}$) is calculated using the Re computed at 426.

At 430, a refined mixture density is determined based on the measured differential pressure, calibrated flow velocity, and the friction coefficient calculated at 428. The difference between the refined mixture density and the previously-calculated mixture density is checked, at 432, to see if the iterative process has converged on a solution. If the difference is greater than a previously determined tolerance value, the operations may be repeated, starting at 416. If the difference is smaller than or equal to the tolerance value, the volumetric phase flow rates ($Q_o$, $Q_w$, and $Q_g$) are calculated at 434.

The iterative calculations associated with the multiphase flow algorithm illustrated by FIG. 4 commence with initially inputted parameters, $WLR^{(0)}$ and $HL^{(0)}$. These parameters represent anticipated WLR and liquid holdup, given geologic conditions or other pertinent variables. Based on these parameters, the processor may compute initial estimates of the density and viscosity of the liquid portion (composed of oil and water only) of the mixture:

$$\rho_L^{(0)} = (1-WLR^{(0)})\rho_o + WLR^{(0)}\rho_w \tag{10}$$

$$\mu_L^{(0)} = (1-WLR^{(0)})\mu_o + WLR^{(0)}\mu_w \tag{11}$$

Furthermore, based on the results of the initial computations in Eqs. 10 and 11, the processor may derive the following initial estimates of mixture density and viscosity:

$$\rho_m^{(0)} = HL^{(0)}\rho_L + (1-HL^{(0)})\rho_g \tag{12}$$

$$\mu_m^{(0)} = HL^{(0)}\mu_L + (1-HL^{(0)})\mu_g \tag{12}$$

Subsequently, the processor may compute an initial estimate of Re ($Re^{(0)}$) using the following formula, where $V_{msrd}$ is the measured bulk velocity of the unknown mixture:

$$Re^{(0)} = \frac{\rho_m^{(0)} V_{msrd} d}{\mu_m^{(0)}} \tag{14}$$

The processor may use the initial estimate of Re to calculate a calibrated velocity ($V_{cal}^{(0)}$). The calculation of calibrated velocity may employ a variety of methods, which may vary depending on the measurement characteristics and accuracy of the bulk velocity sensor. After the calibrated velocity is obtained, the Re is recomputed to improve on the previously calculated Re:

$$Re^{(0)} = \frac{\rho_m^{(0)} V_{cal}^{(0)} d}{\mu_m^{(0)}} \tag{15}$$

Next, the processor calculates an initial estimate of the friction coefficient ($f^{(0)}$) using Chen's Equation, the initially estimated Re, and the surface roughness computed during the calibration process:

$$f^{(0)} = \left[-2\log\left(\frac{1}{3.7065}\left(\frac{\varepsilon}{d}\right) - \frac{5.0452}{Re^{(0)}}\log\left(\frac{1}{2.8257}\left(\frac{\varepsilon}{d}\right)^{1.1098} + \frac{5.8506}{(Re^{(0)})^{0.8981}}\right)\right)\right]^{-2} \tag{16}$$

The friction coefficient may be used to compute an initial estimate of the mixture density:

$$\rho_m^{(0)} = \frac{\Delta p}{\frac{1}{2}(V_{cal}^{(0)})^2 f^{(0)} \frac{L}{d}} \tag{17}$$

Once the initial estimate of mixture density is obtained, the processor may perform iterative steps to refine the initial estimates and initially calculated parameters. Each iteration generates a new calculated mixture density and viscosity, usually different from the value of the previous iteration. When the change from one iteration to the next is less than or equal to a previously determined tolerance value, the iterations cease, with the final calculation being taken as the actual mixture density and viscosity. Typically, the computation time for iterations is less than the time interval between two successive velocity and SoS measurements, leading to zero time lag between the measurement and data processing.

The first iterative step involves a refinement of initial parameters $WLR^{(0)}$ and $HL^{(0)}$. The following equations may be used, where i=1 corresponds to the calculation for the first iteration and i=2, 3, . . . , n for the subsequent iterations.

$$HL^i = \frac{(\kappa_m^{i-1} - \kappa_g)(\rho_w - \rho_o) - (\kappa_w - \kappa_o)(\rho_m^{i-1} - \rho_g)}{(\kappa_w - \kappa_o)(\rho_g - \rho_o) - (\kappa_g - \kappa_o)(\rho_w - \rho_o)} \tag{18}$$

$$WLR^i = \frac{\rho_m^{i-1} - \rho_g + HL^i(\rho_g - \rho_o)}{HL^i(\rho_w - \rho_o)} \tag{19}$$

In Eqs. 18 and 19, $K_o$, $K_w$, $K_g$, and $K_m^{i-1}$ are compressibility factors for the oil phase, water phase, gas phase, and the mixture, respectively. The compressibility factor of a fluid is the inverse of the product of its density and the square of SoS ($K=(\rho \cdot SoS^2)^{-1}$). For the individual phases of oil, water, and gas, the compressibility factors can be computed since the density and SoS of each phase are known for a range of absolute pressure and temperature through the laboratory analysis of bottomhole fluid samples. The compressibility factor of the mixture may also be computed despite the fact that its phase composition is unknown. The density value ($\rho_m^{i-1}$) computed during the previous iteration in conjunction with the measured SoS enable a corresponding mixture compressibility factor ($K_m^{i-1}$) to be obtained.

After refined values $WLR^i$ and $HL^i$ have been calculated, the processor may further obtain a refined calculation of liquid density and viscosity using the following formulas:

$$\rho_L^i = (1-WLR^i)\rho_o + WLR^i\rho_w \tag{20}$$

$$\mu_L^i = (1-WLR^i)\mu_o + WLR^i\mu_w \tag{21}$$

Subsequently, the processor may employ a slip model between liquid and gas phases to account for the velocity differences due to their density contrast in order to derive a refined value of mixture density. In this step, $\lambda_L^{i,slip}$ is defined as the slip holdup that may be obtained from one of any slip modeling techniques, and represents the ratio of the superficial liquid velocity to the calibrated flow velocity. The mixture density and viscosity may then be calculated by the following equations:

$$\rho_m^i = \lambda_L^{i,slip}\rho_L^i + (1-\lambda_L^{i,slip})\rho_g \quad (22)$$

$$\mu_m^i = \lambda_L^{i,slip}\mu_L^i + (1-\lambda_L^{i,slip})\mu_g \quad (23)$$

Additionally, the slip model is used to determine superficial liquid and gas phase velocities ($V_{SL}$ and $V_{Sg}$) which may be different from the bulk velocity of the fluid mixture due to non-homogenous flow conditions. As explained above, these superficial phase velocities represent the velocities which would occur if those phases alone flow in the conduit, and will be used to determine the phase flow rates once the iteration converges. After refined values of $\rho_m^i$ and $\mu_m^i$ have been calculated, a refined Re may be determined using the following equation:

$$Re^i = \frac{\rho_m^i V_{cal}^{i-1} d}{\mu_m^i} \quad (24)$$

In order to calculate a refined friction coefficient, the new Re may be used in conjunction with the surface roughness parameter computed during the initial flow tests in the laboratory. The refined friction coefficient may be computed using Chen's Equation:

$$f^{(i)} = \left[-2\log\left(\frac{1}{3.7065}\left(\frac{\varepsilon}{d}\right) - \frac{5.0452}{Re^{(i)}}\log\left(\frac{1}{2.8257}\left(\frac{\varepsilon}{d}\right)^{1.1098} + \frac{5.8506}{(Re^{(i)})^{0.8981}}\right)\right)\right]^{-2} \quad (25)$$

The refined friction coefficient may be used with the calibrated velocity and measured differential pressure to compute a refined value of mixture density as follows:

$$\rho_m^i = \frac{\Delta p}{\frac{1}{2}(V_{cal}^i)^2 f^i \frac{L}{d}} \quad (26)$$

The value of $\rho_m^i$ may be compared with the value of mixture density calculated during the previous iteration, $\rho_m^{i-1}$. If the change between the two values is less than a previously determined tolerance value, then the iterative process may be terminated after this step. If not, the iterative process may be repeated until the change from the previous iteration to the present iteration satisfies the tolerance check. The tolerance value may be chosen based on accuracy specifications or other criteria.

Once the tolerance value is satisfied and iterations cease, the value $\rho_m^i$ calculated during the final iteration may be used as the value of mixture density. The value of WLR, liquid holdup, superficial liquid velocity, and superficial gas velocity calculated during the final iteration may also be selected for use in subsequent computations which lead to oil, water, and gas phase components (i.e., fractions and flow rates).

In some cases, following the initial determination of the surface roughness parameter through flow loop tests, the material surface characteristics of the flowmeter conduit may change over time. For example, the conduit surface could become rougher or smoother than it was during the initial flow loop tests. In that situation, the initial surface roughness parameter may not yield suitable results. Consequently, the mixture densities calculated by the flowmeter can be expected to become more and more erroneous over time, as a function of the rate at which the flowmeter conduit becomes smoother or rougher.

According to certain aspects, changes in surface roughness may be accounted for by performing subsequent laboratory tests. The subsequent tests may be done using a fluid flow of known density and employ the same computational method as executed in the initial laboratory tests. When a subsequent test is performed, the newly calculated $\epsilon$ parameter is thereafter employed in place of the previous $\epsilon$ parameter. The new $\epsilon$ parameter may thereafter be employed to calculate the mixture density of subsequent flows using the iterative technique explained above.

Figure 5:
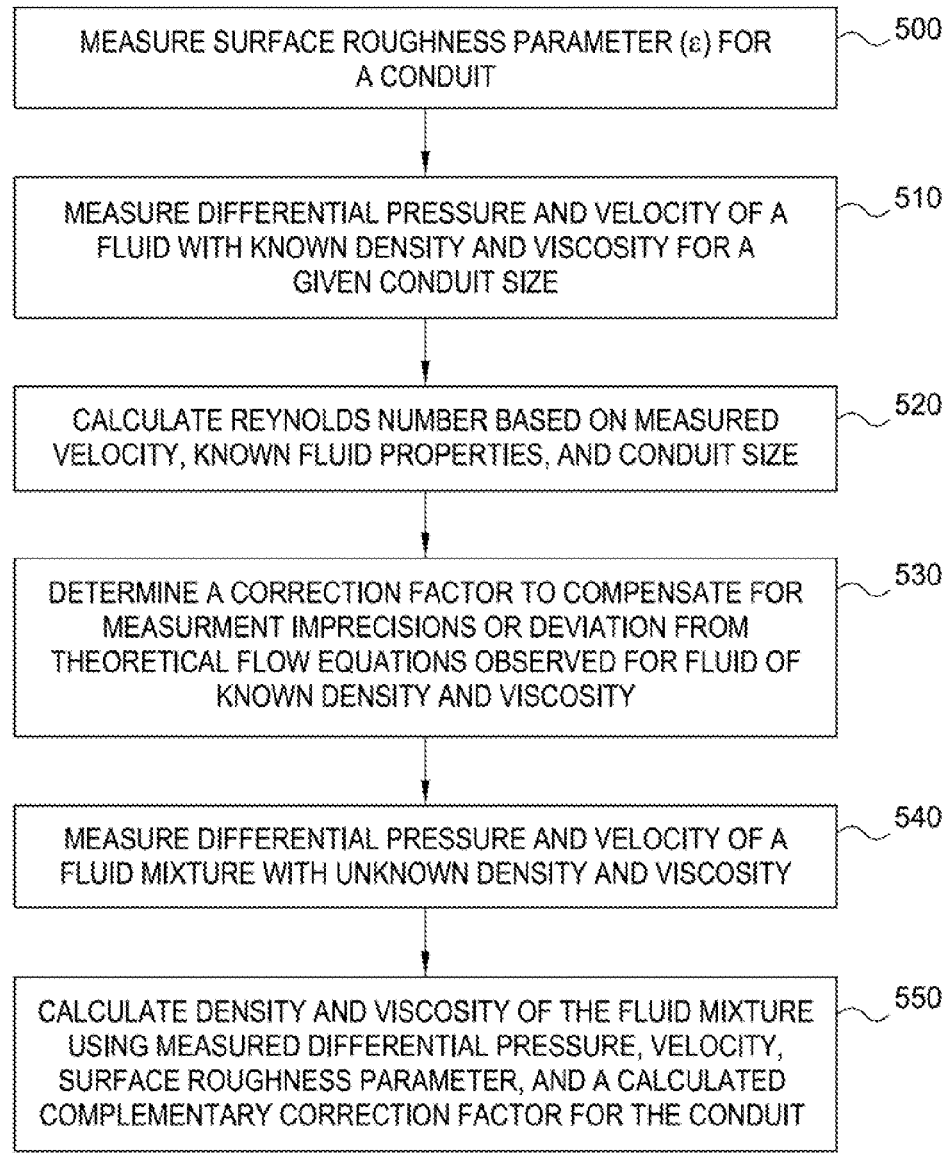
FIG. 5 is a flow diagram illustrating example alternative operations for determining density, in accordance with embodiments of the present disclosure.

FIG. 5 illustrates an alternative approach that may be used to enable the calculation of mixture density, WLR, liquid holdup, superficial liquid velocity, and superficial gas velocity. At 500, the surface roughness parameter ($\epsilon$) of the flowmeter conduit is measured using any of various suitable devices, such as electromechanical or optical devices. At 510, the bulk velocity and differential pressure of a fluid of known density and viscosity are measured. At 520, the Re is calculated using the measured and known quantities in accordance with the relationship provided above. At 530, a correction factor is determined in an effort to compensate for measurement imprecision in the surface roughness parameter or deviation from theoretical flow equations observed for a fluid of known density and viscosity.

At 540, the flowmeter measures velocity and differential pressure during flow of a different fluid of unknown density and viscosity. At 550 the flowmeter calculates density and viscosity of this fluid using the measured differential pressure, the calibrated flow velocity, the measured surface roughness parameter, and the correction factor for the conduit.

The embodiment depicted by the flow diagram in FIG. 5 may be capable of even more accurate measurements of mixture density because the surface roughness parameter ($\epsilon$) of the flowmeter's conduit is measured using laboratory instruments or other electromechanical or optical techniques. This embodiment is premised on the practical recognition that measured values under conditions of actual fluid flow may not perfectly conform to the theoretical relationship expressed in Eq. 8. In other words, during the initial flow loop tests with a fluid flow of known density and viscosity, inevitable measurement imprecision may result in $$\Delta P_{msrd} \neq \left(\frac{1}{2}\rho_{m,known}V_{cal}^2\right)\left(\frac{L}{d}\right)f_{known} \quad (27)$$

where $\Delta P_{msrd}$ is the measured differential pressure, $V_{cal}$ is the measured-and-calibrated bulk velocity of the fluid flow, $f_{known}$ is the friction factor determined by Eq. 6 when the measured surface roughness parameter ($\epsilon_{msrd}$) applied, and $\rho_{m,known}$ is the known density of the fluid mixture.

A correction factor (which may also be referred to as a "complementary factor") is calculated to compensate for these discrepancies, which may be expected to persist when the flowmeter is later used to calculate the density of unknown fluid mixture flows. There are different ways to determine and employ such a correction factor. One example is to find a correction factor value ($f_{correction}$) that satisfies the following equation when the bulk velocity and differential pressure measured during the fluid flow of known density are applied:

$$\Delta P_{msrd} = \left(\frac{1}{2}\rho_{m,known}V_{cal}^2\right)\left(\frac{L}{d}\right)(f_{known} + f_{correction}) \quad (28)$$

Alternatively, Eq. 28 may be thought of as modeling the measured pressure drop by superposing two components: the first component is based on the standard theoretical approach, whereas the second component is the deviation from what the measured pressure drop should be. Thus, $$\Delta P_{msrd} = \Delta P_{friction} + \Delta P_{correction} \quad (29)$$

This deviation may be corrected or "complemented" so that the density of unknown fluid mixtures may be predicted within the measurement precision of the differential pressure and velocity sensors. For certain conduits, during subsequent flows of unknown mixture density ($\rho_m$), the previously calculated correction factor ($f_{correction}$) may be expected to continue to relate the fluid flow parameters in the following manner:

$$\Delta P_{msrd} = \left(\frac{1}{2}\rho_m V_{cal}^2\right)\left(\frac{L}{d}\right)(f_{known} + f_{correction}) \quad (30)$$

Figure 6:
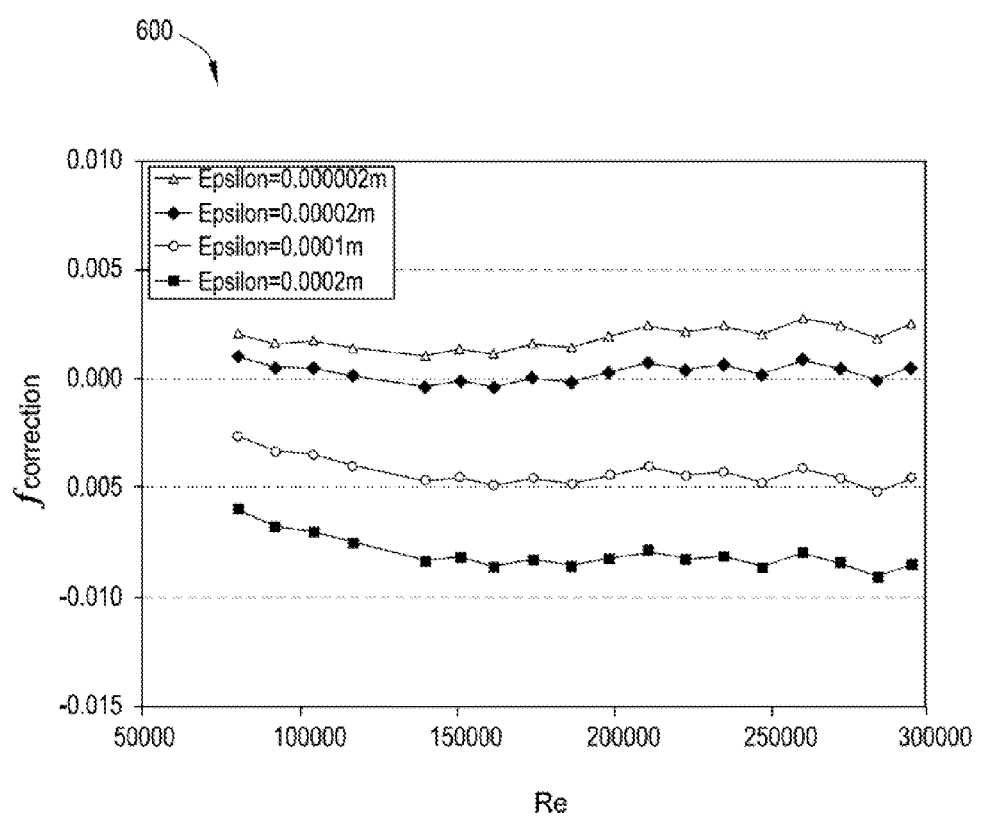
FIG. 6 shows variation of a friction coefficient correction factor ($f_{correction}$) as a function of Reynolds number (Re) for different surface roughness values, in accordance with embodiments of the present disclosure.
Figure 7:
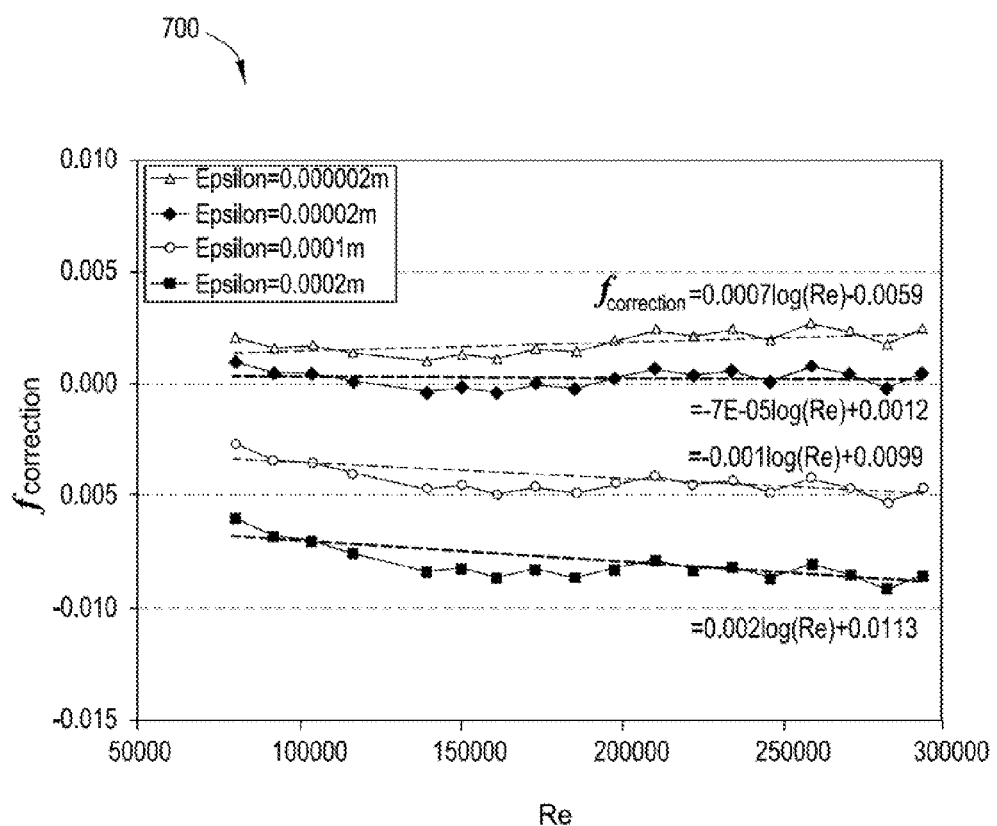
FIG. 7 shows how a friction coefficient correction factor can be curve-fit as a function of Re for a given surface roughness, in accordance with embodiments of the present disclosure.

FIG. 6 is a graph 600 illustrating example correction factors determined using Eq. 30 applied to flows of known density for various Reynolds numbers. Additionally, the example correction factors are shown for various conduits, each of which is characterized by a unique surface roughness parameter (epsilon, or $\epsilon$). As illustrated by FIG. 6, the correction factors for conduits may vary. FIG. 7 is a graph 700 depicting an example regression of the correction factor values of FIG. 6 as a function of Reynolds numbers for different surface roughness parameters. For this example regression function, all the correction factors can be represented by the following equation family:

$$f_{correction} = \frac{1}{K}\log(Re) + A \quad (31)$$

where K and A are constants for a given value of surface roughness. Other representations based on Re are also possible.

Figure 8:
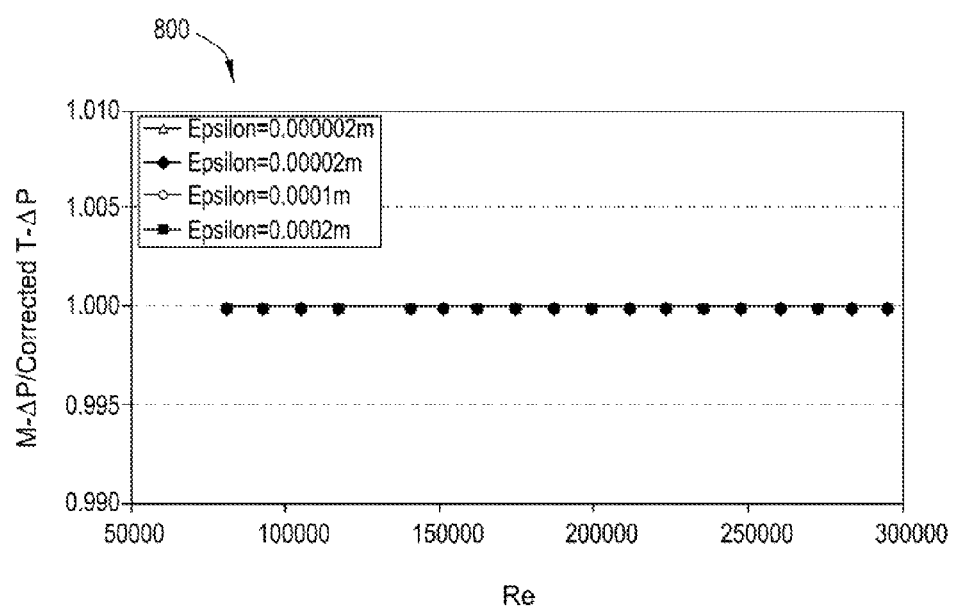
FIG. 8 is a graph of a ratio of measured to theoretical differential pressure versus Re after correction, in accordance with embodiments of the present disclosure.

FIG. 8 is a graph 800 illustrating the use of Eq. 30 with example results of corrections made to theoretical pressure drop by making use of correction friction factors as determined by Eq. 31. The graph 800 demonstrates that once the correction is implemented, the theoretical and measured differential pressures align (i.e., the ratio of measured differential pressure to corrected theoretical differential pressure is 1.000 across the Reynolds numbers).

Figure 9:
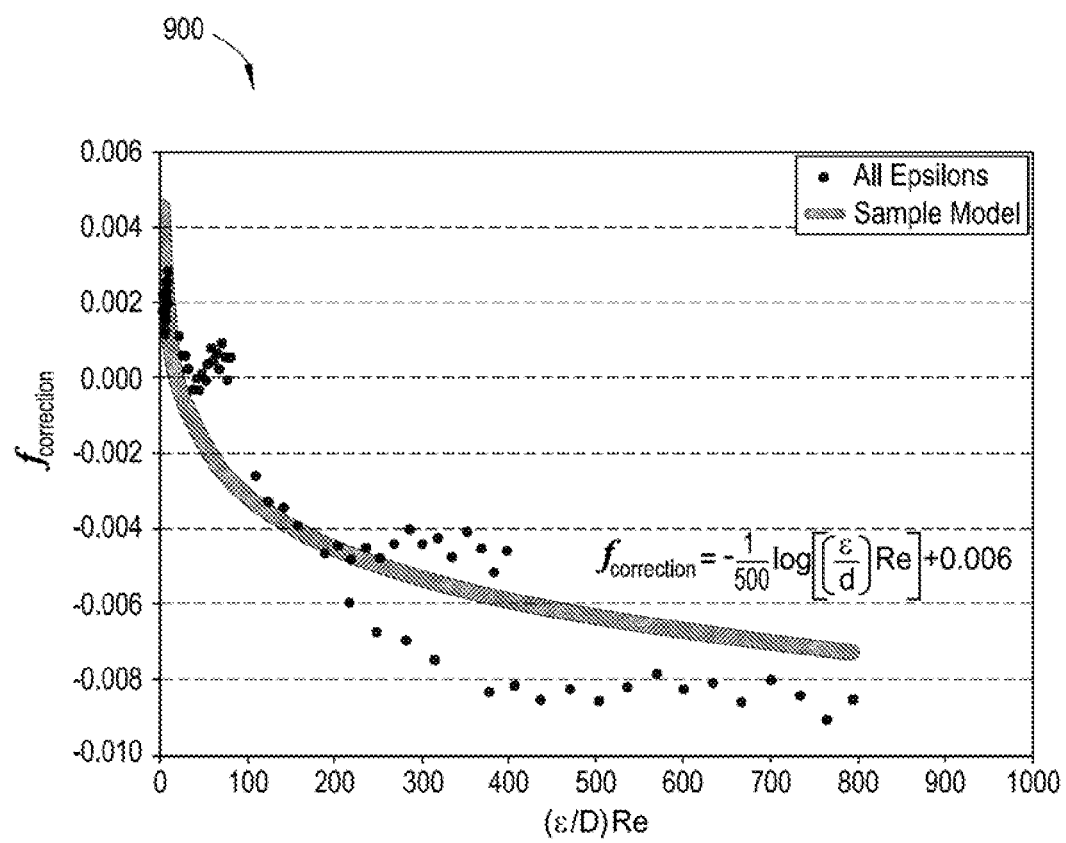
FIG. 9 shows a curve-fit regression function that may approximately predict correction factors for a range of surface roughness values when plotted against a different function involving Re, in accordance with embodiments of the present disclosure.

FIG. 9 is a graph 900 consolidating the data displayed in the graphs of FIGS. 6 and 7. A curve-fit regression function may approximately predict correction factors for a range of surface roughness values when plotted against a functional form of $(\epsilon/d)\cdot Re$. One such example of the regression curve depicted in the figure may be represented by the following equation family:

$$f_{correction} = \frac{1}{M}\log\left[\left(\frac{\varepsilon}{d}\right)Re\right] + B \quad (32)$$

where M and B are constants for a group of surface roughness values.

When Eq. 30 is applied to subsequent flows of unknown density, it may be combined with Eq. 9 to yield the following relationship:

$$\Delta P_{msrd} = \left(\frac{1}{2}\rho m V_{cal}^2\right)\left(\frac{L}{d}\right) \quad (33)$$

$$\left(\left[-2\log\left(\frac{1}{3.7065}\left(\frac{\varepsilon}{d}\right) - \frac{5.0452}{Re}\log\left(\frac{1}{2.8257}\left(\frac{\varepsilon_{msrd}}{d}\right)^{1.1098} + \frac{5.8506}{Re^{0.8981}}\right)\right)\right]^{-2} + f_{correction}\right)$$

Thus, for fluid flows of unknown mixture density, the mixture density $\rho_m$ may be reliably calculated by measuring $\Delta P$ and V and applying the measured value of $\epsilon_{msrd}$ and the calculated value $f_{correction}$ to the procedures and formulas associated with the iterative multiphase flow diagram of FIG. 4 described above. In the iterative process, all calculations remain the same, with the exception that the friction coefficient (f) in Eqs. 17 and 26 is substituted by f+$f_{correction}$ in the same manner as illustrated in Eq. 33. As described previously, after $\rho_m$ has been calculated, the processor proceeds to calculate phase fractions and volumetric phase flow rates in accordance with the methods described above.

Figure 10:
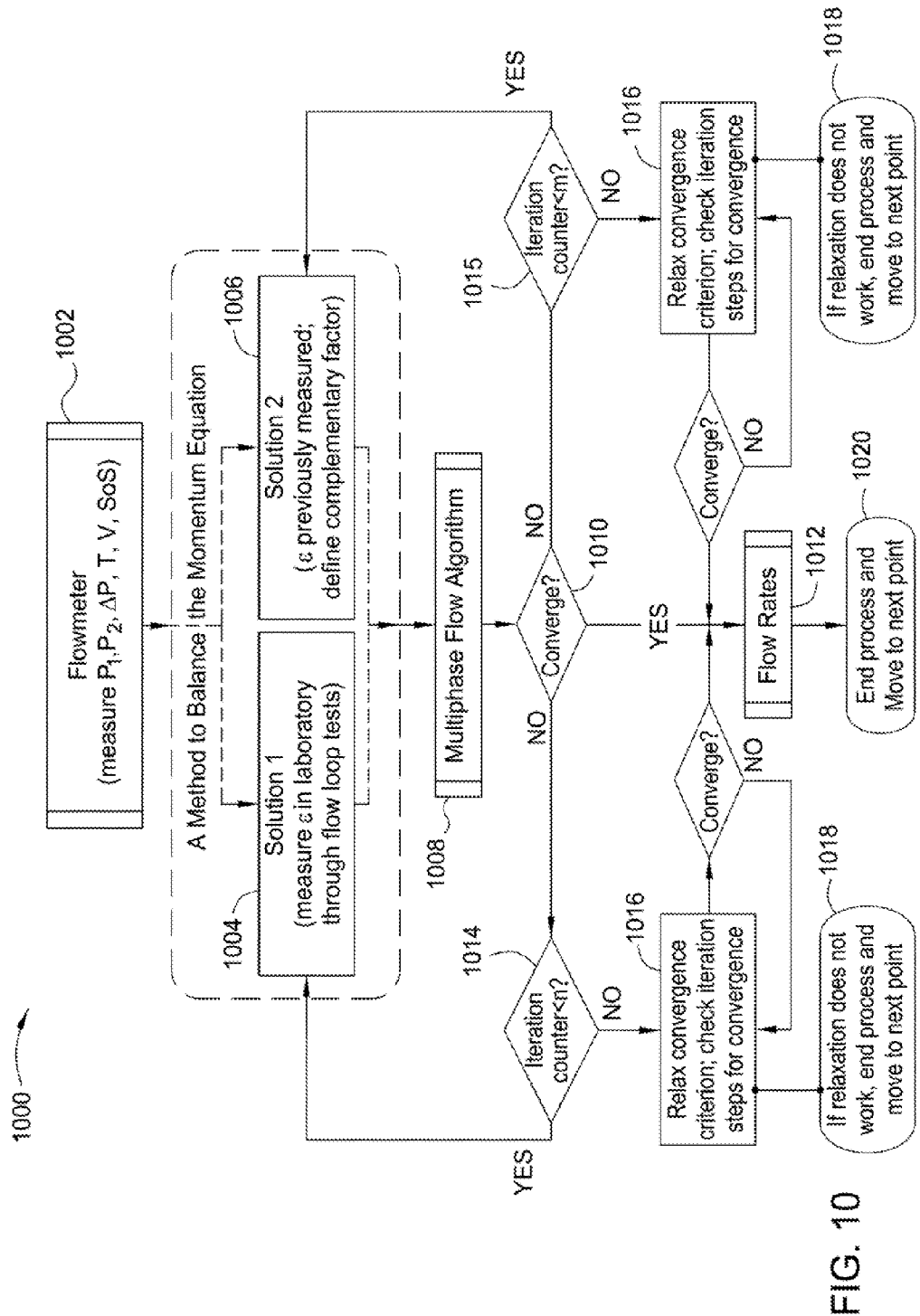
FIG. 10 is a flow diagram illustrating example operations for determining phase flow rates by balancing the momentum equation using two different solutions, in accordance with embodiments of the present disclosure.

FIG. 10 summarizes example operations 1000 for measuring multiphase flow, in accordance with embodiments of the present disclosure, including operations associated with two of the techniques illustrated above. At 1002, absolute pressure, differential pressure across the conduit (or a second absolute pressure across the conduit to obtain a differential pressure when used in conjunction with the first absolute pressure), absolute temperature, bulk velocity of the fluid flow, and SoS of the fluid mixture are measured in accordance with the techniques described above with respect to FIG. 1.

As described above, if surface roughness of the conduit has not been previously measured (using any of various suitable techniques), the processor employs, at 1004, a value of surface roughness determined during initial flow loop tests. Subsequently, an iterative process, which involves multiphase flow algorithm calculations (described above with respect to FIG. 4) to determine the density of the fluid mixture starts at 1008. If a convergence criterion is satisfied at 1010, then the most recently calculated value of mixture density is used to calculate phase flow rates at 1012. At 1020, the process ends for the current data point and then moves to the next point.

If convergence does not occur, the processor commences another iterative step through 1004 provided the iteration counter at 1014 is smaller than a predetermined value (n). The process may be repeated until convergence is reached. If convergence does not occur at 1010 and the iteration counter at 1014 is equal to the predetermined value of n, the convergence criterion is progressively relaxed at 1016 followed by checking the previous iteration steps for convergence. Once convergence occurs, the flow rates are calculated at 1012. If convergence still does not occur after the predetermined relaxation allowance, the process ends for the current data point at 1018 (i.e., no solution is found) and then moves to the next acquired data point.

If surface roughness has previously been measured using laboratory instruments or other electromechanical techniques, a correction factor may be employed at 1006. Subsequently, an iterative process, which involves multiphase flow algorithm calculations to determine the mixture density, begins at 1008. If a convergence criterion is satisfied at 1010, then the most recently calculated value of mixture density is used to calculate phase flow rates at 1012. At 1020, the process ends for the current data point and then moves to the next point.

If convergence does not occur, the processor may commence another iterative step through 1006 provided the iteration counter at 1015 is smaller than a predetermined value (m), which may be different than or equal to n. The process may be repeated until convergence is reached. If convergence does not occur at 1010 and the iteration counter at 1014 is equal to the predetermined value of m, the convergence criterion is progressively relaxed at 1016 followed by checking the previous iteration steps for convergence. Once convergence occurs, the flow rates are calculated at 1012. If convergence still does not occur after the predetermined relaxation allowance, the process ends for the current data point at 1018 (i.e., no solution is found) and then moves to the next acquired data point.

Any of the operations described above, such as the operations 1000, may be included as instructions in a computer-readable medium for execution by the control unit 116 or any other processor. The computer-readable medium may comprise any suitable memory or other storage device for storing instructions, such as read-only memory (ROM), random access memory (RAM), flash memory (e.g., a flash drive with a universal serial bus (USB) interface), an electrically erasable programmable ROM (EEPROM), a compact disc ROM (CD-ROM), a digital versatile disc ROM (DVD-ROM), or a floppy disk.

Solution Domain of the System

Figure 11:
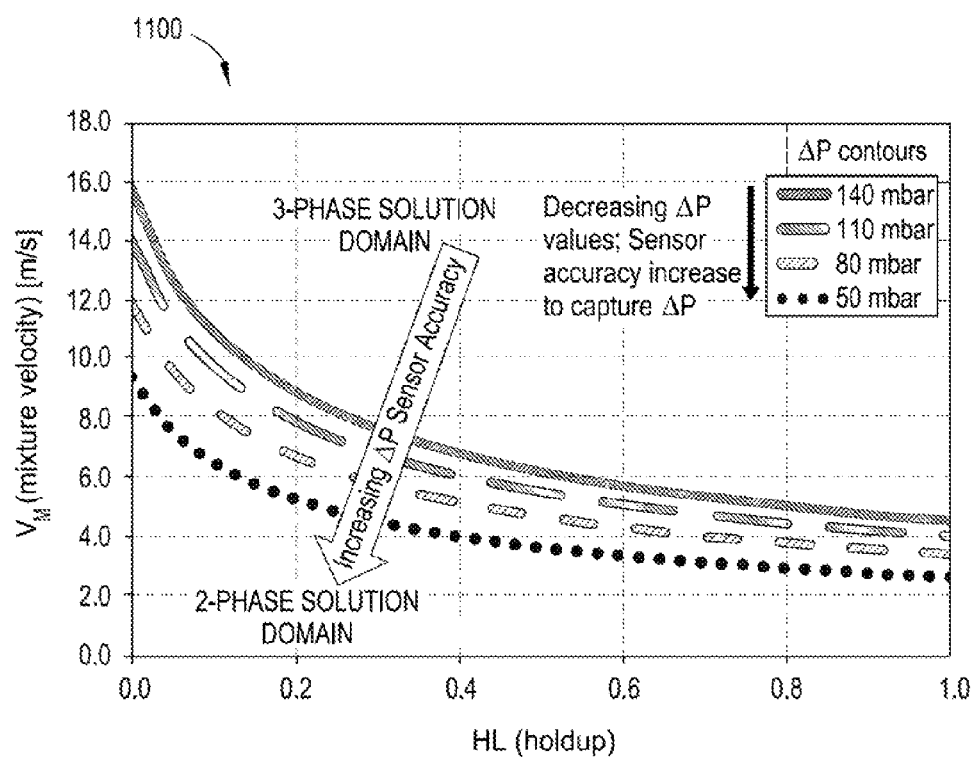
FIG. 11 illustrates variations of 3-phase and 2-phase solution domains with differential pressure (ΔP) measurement accuracy, in accordance with embodiments of the present disclosure.

The graph 1100 in FIG. 11 illustrates the variations of 3-phase and 2-phase solution domains with varying mixture velocity and holdup for a given water-in-liquid ratio (WLR), a distance (L) between two pressure ports, a pipe inner diameter (d), a pipe surface roughness ($\epsilon$), and the density and viscosity values of individual phases. The graph 1100 may also be used to determine when the system described herein is expected to measure 3-phase flow.

The hyperbolic contours in the graph 1100 correspond to the theoretical differential pressures given by the right-hand side of Eq. 8 or, more explicitly, Eq. 9. The contours can be obtained by systematically varying the holdup (the amount of liquid in an oil/water/gas mixture) and finding the corresponding mixture velocity for a given $\Delta P$ value. The steps involve calculating the mixture density and viscosity based on the individual phase properties, given WLR and assumed holdup using Eqs. 12 and 13, and iteratively solving Eq. 9 for the mixture velocity, which is found in the right-hand side of Eq. 9 in explicit and implicit (Re) forms. This is done in such a way that the right-hand side of Eq. 9 always equals the same value for a given contour. A hyperbolic variation of contours is expected since the differential pressure between the measurement ports is directly proportional to the flowing fluid density and the velocity square of the flow, and so, the denser liquid phase will create the same pressure differential at lower velocities as the gas phase, as can be justified by Eq. 8 and seen from the graph 1100. Consequently, if the liquid phase is dominant in a gas/liquid mixture (i.e., liquid-rich flows), relatively lower velocities would be sufficient to create the same differential pressure due to the denser fluid mixture. In contrast, gas-rich flows may typically involve relatively higher velocities for the same differential pressure due to their decreased fluid density. Different contours can be obtained by starting with different mixture velocities and systematically varying the amount of liquid in the mixture. In the graph 1100, there are four different such contours with the theoretical differential pressures ranging from 140 mbar (the top contour) to 50 mbar (the bottom contour).

The differential pressure sensor 108 is expected to measure the $\Delta P$ (given in the left-hand side of Eq. 8 or Eq. 9) caused by the frictional pressure loss due to the flowing mixture (right-hand side of Eq. 8). However, as in any sensor, the differential pressure sensor has an accuracy which may be a function of its design and calibration characteristics. This, in turn, means that there exists a differential pressure value below which the differential pressure sensor cannot make a meaningful measurement, even though a theoretical meaningful differential pressure exists due to the motion of the fluid.

Combining the two sides of Eq. 8 with the graph 1100, one may always find a differential pressure contour which characterizes the accuracy of a given differential pressure sensor. It is then assumed that when the frictional pressure drop is above the accuracy value of the sensor, the $\Delta P$ measurement by the sensor is meaningful. The hyperbolic contour that characterizes the sensor accuracy determines the boundary between the 3-phase and 2-phase solutions shown in the graph 1100. The regions above these hyperbolic "$\Delta P$ sensor accuracy" contours represent the 3-phase domains (because the sensor can make meaningful $\Delta P$ measurements), while those regions below the contours represent the 2-phase domains (because the sensor cannot make meaningful $\Delta P$ measurements).

Finally, if the measurement system is not horizontal (i.e., the flowmeter has an inclination angle in the well), this would increase the value of the differential pressure between the measurement ports due to the added hydrostatic pressure caused by the elevation difference (Eq. 4). In this case, the 3-phase solution domain will be greater, and the system may perform better.

Aspects and Advantages of the In-Well Multiphase Flowmeter

The challenges associated with in-well multiphase flow measurement are numerous. Consequently, there are not many technologies available for this challenging task. One approach that has been used is a Venturi-based solution in which the Venturi is combined with other technologies. However, it is well-known that Venturi-based solutions have some fundamental issues in a downhole, multiphase environment. First, the solution is not full-bore, and the primary design causes significant pressure loss due to the restriction of the flow. This restriction may also prevent some well operations, and as a result, this is usually not a preferred solution by operators. Second, the solution is based on electronic technology, which is not suitable for severe in-well conditions. The lifetimes of electronic gauges, as well as the drift in their measurements, are also some of the primary reasons that these meters are not frequently used.

There is, however, an increasing trend in designing "intelligent completions" in which the well is equipped with in-flow control valves (ICVs) or in-flow control devices (ICDs) so that the well production may be optimized (or at least so that well production efficiency may be increased) by creating an even flow distribution particularly for multi-zone applications. To achieve this, the flow in the well may be measured for the life of the well. It is clear that there is a gap between what is expected from in-well flow measurement and what is currently offered. Embodiments of the present disclosure represent an attempt to close this gap and provide significant advantages over existing flow measurement solutions. Some of these advantages are listed below:

Non-Intrusive:

Most multiphase flowmeters include a Venturi component as the primary design, which causes significant pressure loss due to the restriction of the flow. Furthermore, the potential impingement of sand (or other solid content that could be present in the flow) on the converging Venturi section coupled with the flow dynamic pressure may cause erosion and corrosion in the material and change the characteristics of the Venturi over time. As a result, the performance is adversely affected. Embodiments of the present disclosure do not have any obstruction or area change; thus, the erosion and corrosion are insignificant, if any. Accordingly, the performance is not affected over time.

Optical:

For some embodiments, the in-well flowmeter is based on fiber-optic technology and does not have the shortcomings of the electronic-based sensors from reliability, survivability, and longevity perspectives. The relatively shorter lifetimes of electronic equipment, as well as the drift in their measurements, are the primary reasons that some flowmeters also have retrievable versions or redundant sensor arrangements, which increase the cost significantly.

Non-Nuclear:

Many flowmeters have gamma-ray detectors that are based on nuclear technology. Such detectors introduce regulatory concerns, potential export/import difficulties, and special training requirements, as well as potential liability issues. Furthermore, these devices are not immune to failures. One less obvious disadvantage of nuclear-based tools is their lifetime. For example, Cesium-137, which is frequently used in these devices, has a half-life of 30 years. Manufacturers often quote a useable lifetime of only 15 years. In contrast, embodiments of the present disclosure are based on robust and field-proven turbulent flow measurements and eliminate all the issues pertinent to nuclear devices.

Zonal Measurement:

One of the main advantages of embodiments disclosed herein is their ability to determine zonal production rates in multi-zone applications. The in-well optical flowmeter may be placed in each zone, or a combination of flowmeters may be arranged in an efficient way to determine the contribution of each zone, as well as the total contribution of the well. Today's intelligent completions use ICDs or ICVs to achieve evenly distributed flow, especially along horizontal wells, in an effort to avoid or at least reduce production problems including water or gas coning and sand production. Flowmeters installed in a multi-zone application provide the phase flow rates that can be used to determine the optimum settings for ICVs, which help optimize the production in real-time.

Bidirectional Measurement:

The bidirectional flow measurement capability of the optical flowmeter is also a testament to the robustness of the technology on which it is based. True to the "intelligent completion" concept, it is possible to detect cross-flow between different zones or to change service from producer to injector regardless of the type of fluid injected (liquid or gas) with no hardware/software changes. The bidirectional flow measurement is a unique feature that most other flow measurement technologies are not capable of doing, even at the surface.

High Turndown Ratio:

Unlike the limited flow rate range of differential pressure measurement devices such as a Venturi, embodiments of the present disclosure do not have a practical high limit. Embodiments of the present disclosure can easily surpass a turndown ratio of 30, about three times more than a Venturi. The flowmeter is a part of the tubing with no flow blockage. Therefore, when the high limit is reached, it is not because of the measurement limit of the meter, but because of the frictional losses in the entire tubing due to high velocities.

Conclusion

Embodiments of the present disclosure represent a significant development for in-well multiphase flow measurement in any orientation. Currently, an optical flowmeter three-phase solution is available only for vertical or near-vertical in-well applications. The capability introduced herein represents a more robust approach and removes the limitation of a "vertical" or "near-vertical" orientation. It is relatively easy to implement within the body of the flowmeter: not only does this make the approach more convenient for different applications, but it also provides an independent arrangement from the rest of the pipeline. This is in contrast to a conventional vertical solution, in which a secondary P/T gauge is installed with significant separation (e.g., 50 m to 100 m), which may create potential issues from a completion perspective. Embodiments of the present disclosure may entail determining the pressure drop across the length of the flowmeter as precise as possible. The pressure drop may be measured by two independent pressure gauges for some embodiments, or a ΔP transducer may be used for this task in other embodiments.

While the foregoing is directed to embodiments of the present disclosure, other and further embodiments may be devised without departing from the basic scope thereof, and the scope thereof is determined by the claims that follow.

What is claimed is:

1. A method for determining one or more flow rates of phase components of a fluid mixture flowing in a conduit, comprising:
    calculating or measuring a surface roughness parameter associated with the conduit;
    measuring a bulk velocity and a speed of sound of the fluid mixture;
    determining a differential pressure between two points in the conduit;
    calculating, by a processor, a density of the fluid mixture as a function of the differential pressure, the bulk velocity, and the surface roughness parameter associated with the conduit, wherein calculating the density comprises utilizing one or more theoretical fluid flow relationships that relate differential pressure of a fluid flow to bulk velocity, density, and a friction coefficient of the conduit based on the surface roughness parameter; and
    calculating at least one of phase fractions or the one or more flow rates of the phase components of the fluid mixture, using the speed of sound, the bulk velocity, and the calculated density.

2. The method of claim 1, wherein the surface roughness parameter associated with the conduit was previously calculated based on differential pressure and bulk velocity measurements for a fluid flow having a known density.

3. The method of claim 2, further comprising:
    periodically measuring differential pressure and velocity for the fluid flow having the known density; and
    updating the surface roughness parameter associated with the conduit based on the periodically measured differential pressure and velocity.

4. The method of claim 2, further comprising:
    storing data regarding a change in the surface roughness parameter over time; and
    adjusting a previously determined surface roughness parameter as a function of the elapsed time since the surface roughness parameter was last determined.

5. The method of claim 1, wherein the surface roughness parameter associated with the conduit was previously measured using a roughness measuring device.

6. The method of claim 5, wherein calculating the density of the fluid mixture comprises calculating a correction factor for the conduit to compensate for a discrepancy between measured fluid flow parameters and theoretical equations relating the parameters.

7. The method of claim 1, wherein the phase components comprise individual oil, gas, and water phases.

8. The method of claim 1, wherein the conduit is horizontally oriented.

9. An apparatus for determining one or more flow rates of phase components of a fluid mixture in a conduit, comprising:
a processing system configured to:
calculate or measure a surface roughness parameter associated with the conduit;
determine a bulk velocity and a speed of sound of the fluid mixture;
determine a differential pressure between two points in the conduit;
calculate a density of the fluid mixture as a function of the differential pressure, the bulk velocity, and the surface roughness parameter associated with the conduit, wherein the processing system is configured to calculate the density of the fluid mixture by utilizing one or more theoretical fluid flow relationships that relate differential pressure of a fluid flow to bulk velocity, density, and a friction coefficient of the conduit based on the surface roughness parameter; and
calculate at least one of phase fractions or the one or more flow rates of the phase components of the fluid mixture, using the speed of sound, the bulk velocity, and the calculated density; and
a memory coupled to the processing system.

10. The apparatus of claim 9, wherein the surface roughness parameter associated with the conduit was previously calculated based on differential pressure and bulk velocity measurements for a fluid flow having a known density.

11. The apparatus of claim 10, wherein the processing system is further configured to:
periodically determine differential pressure and velocity for the fluid flow having the known density; and
update the surface roughness parameter associated with the conduit based on the periodically determined differential pressure and velocity.

12. The apparatus of claim 10, wherein the memory is configured to store data regarding a change in the surface roughness parameter over time and wherein the processing system is configured to adjust a previously determined surface roughness parameter as a function of the elapsed time since the surface roughness parameter was last determined.

13. The apparatus of claim 9, wherein the surface roughness parameter associated with the conduit was previously measured using a roughness measuring device.

14. The apparatus of claim 13, wherein the processing system is configured to calculate the density of the fluid mixture by calculating a correction factor for the conduit to compensate for a discrepancy between measured fluid flow parameters and theoretical equations relating the parameters.

15. The apparatus of claim 9, wherein the phase components comprise individual oil, gas, and water phases.

16. A non-transitory computer-readable medium for determining one or more flow rates of phase components of a fluid mixture flowing in a conduit, comprising instructions which, when executed by a processing system, perform operations including:
calculating or measuring a surface roughness parameter associated with the conduit;
measuring a bulk velocity and a speed of sound of the fluid mixture;
determining a differential pressure between two points in the conduit;
calculating a density of the fluid mixture as a function of the differential pressure, the bulk velocity, and the surface roughness parameter associated with the conduit, wherein calculating the density comprises utilizing one or more theoretical fluid flow relationships that relate differential pressure of a fluid flow to bulk velocity, density, and a friction coefficient of the conduit based on the surface roughness parameter; and
calculating at least one of phase fractions or the one or more flow rates of the phase components of the fluid mixture, using the speed of sound, the bulk velocity, and the calculated density.

17. The non-transitory computer-readable medium of claim 16, wherein the surface roughness parameter associated with the conduit was previously calculated based on differential pressure and bulk velocity measurements for a fluid flow having a known density.

18. The non-transitory computer-readable medium of claim 16, wherein the surface roughness parameter associated with the conduit was previously measured using a roughness measuring device.

* * * * *